(12) United States Patent
Kimizuka et al.

(10) Patent No.: US 6,576,679 B2
(45) Date of Patent: Jun. 10, 2003

(54) HYDROGEL

(75) Inventors: Nobuo Kimizuka, 701, 1-11 Kashiihama 4-Chome Higashi-ku Fukuoka-ken (JP); Takuya Nakashima, Higashi-ku (JP); Kazuhiro Kagawa, Wako (JP)

(73) Assignees: Honda Giken Kogyo Kabushiki Kaisha, Tokyo (JP); Nobuo Kimizuka, Fukuoka-ken (JP)

( * ) Notice: Subject to any disclaimer, the term of this patent is extended or adjusted under 35 U.S.C. 154(b) by 0 days.

(21) Appl. No.: 09/954,954

(22) Filed: Sep. 18, 2001

(65) Prior Publication Data

US 2002/0065329 A1 May 30, 2002

(30) Foreign Application Priority Data

Sep. 18, 2000 (JP) ........................................ 2000-282486

(51) Int. Cl.$^7$ .......................... A61K 9/10; A61K 31/16; A01N 25/04
(52) U.S. Cl. ...................... 516/102; 516/103; 516/900; 514/613; 514/626; 514/944; 424/450
(58) Field of Search ................................. 516/102, 103, 516/900; 514/613, 626, 944; 424/450

(56) References Cited

U.S. PATENT DOCUMENTS

| | | | | |
|---|---|---|---|---|
| 3,048,552 A | * | 8/1962 | Fang | 523/400 |
| 3,684,596 A | * | 8/1972 | Vercauteren | 149/40 |
| 4,018,689 A | * | 4/1977 | Thompson | 516/102 |
| 4,299,740 A | * | 11/1981 | Messenger et al. | 516/102 |
| 4,585,572 A | * | 4/1986 | Lane et al. | 516/102 |
| 5,092,976 A | * | 3/1992 | Hossain et al. | 204/242 |
| 5,965,258 A | | 10/1999 | Riess et al. | 428/364 |

FOREIGN PATENT DOCUMENTS

| JP | 06-157561 | 6/1994 |
|---|---|---|
| JP | 2000-126585 | 5/2000 |

OTHER PUBLICATIONS

Kimizuka et al., "Bilayer Membranes of Four–Chained Ammonium Amphiphiles", Chemistry Letters, No. 1, Jan. 1990, pp. 29–32.*

Asano et al., "Adsorption of a Soluble Dye Polymer onto Spread Monolayers", Langmuir, Dec. 1993, vol. 9, No. 12, pp. 3587–3593.*

Kimizuka et al., "AFM Observation of Organofel Nanostructures on Graphite in the Gel–Assisted Transfer Technique", Chemistry Letters, No. 10, Oct. 1998, pp. 967–968.*

* cited by examiner

Primary Examiner—Daniel S. Metzmaier
(74) Attorney, Agent, or Firm—Lahive & Cockfield, LLP

(57) ABSTRACT

A hydrogel formed by adding an anion having a molecular weight of 90 or more to an aqueous dispersion of a cationic amphiphile comprising a linear or branched alkyl group having 10 or less carbon atoms in a hydrophobic moiety. The hydrogel has a network having a bilayer-membrane, nanofiber structure and undergoes a reversible gel-sol transformation.

5 Claims, 2 Drawing Sheets

HYDROGEL

FIELD OF THE INVENTION

The present invention relates to a hydrogel based on a low-molecular weight compound, particularly to a supramolecular hydrogel subjected to a reversible gel-sol phase transformation.

PRIOR ART

Conventional soft materials represented by hydrogels are mainly composed of synthetic polymers or biopolymers such as polysaccharides. However, in order to control the structures and properties such as substance-holding capacity and permeability of the hydrogels on a molecular (nano) level, the nano-structures and surface chemical structures of the gels should be accurately controlled, and this poses a technical limitation on the conventional polymer-based hydrogels. These issues hold a key to impart new functions such as high-speed stimulus response and chemical-mechanical energy conversion, etc. to the hydrogels.

On the other hand, if a new method were devised to form hydrogels of nano-level supramolecular assemblies by self-assembling low-molecular weight compounds, it would be possible to accurately control their nano-structures and properties through the chemical structure of constituent molecules and the characteristics of supramolecular assemblies (phase transformation phenomenon, etc.).

The development of a supramolecular hydrogel using a low-molecular weight compound needs the development of an artificial supramolecular assembly that spontaneously forms a hydrogel. Though there are a lot of known examples of organogelators that can be self-organized in an organic solvent to form a gel, supramolecular assemblies capable of forming a gel in an aqueous solution in a self-organizing manner are not known at present with respect to their general molecular design.

OBJECT OF THE INVENTION

Accordingly, an object of the present invention is to provide a supramolecular hydrogel based on a compound having a relatively low molecular weight, which is synthesized according to the molecular design of synthetic bilayer membranes.

SUMMARY OF THE INVENTION

As a result of intense research in view of the above object, the inventors have found that a supramolecular hydrogel can be obtained from a low-molecular weight compound, by adding an anion having a molecular weight of 90 or more to an aqueous dispersion of a cationic amphiphile comprising a linear or branched alkyl group having 10 or less carbon atoms in a hydrophobic moiety. The present invention is based on this finding.

Thus, the hydrogel of the present invention comprises a combination of a cationic amphiphile comprising a linear or branched alkyl group having 10 or less carbon atoms in its hydrophobic moiety and an anion having a molecular weight of 90 or more.

The cationic amphiphile used in the present invention comprises a hydrocarbon moiety that is a low-molecular weight compound having 10 or less carbon atoms, differing from the conventional molecules forming bilayer membranes that comprise highly crystalline, long-chain alkyl groups, etc., in their hydrophobic moieties. Because the cationic amphiphile used in the present invention has lower molecular orientation than the general molecules forming bilayer membranes, it cannot form a hydrogel without combination with other compounds. However, it can form a stable hydrogel when combined with anions having a molecular weight of 90 or more.

DESCRIPTION OF THE PREFERRED EMBODIMENTS

[A] Cationic Amphiphile

Figure 1:
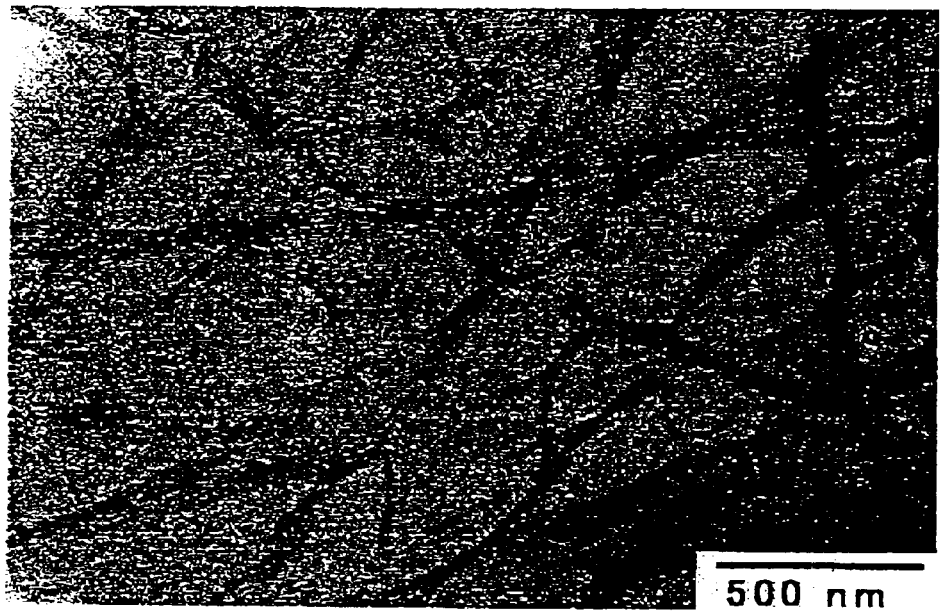
FIG. 1 is an electron photomicrograph of a sample comprising Compound 2 mixed with $ClO_4^-$ (10 mM), which was diluted to 1 mM.

The cationic amphiphile used in the present invention comprises a hydrophobic moiety and a hydrophilic moiety, and the hydrophobic moiety comprises a linear or branched alkyl group having 10 or less carbon atoms. A cation group in the cationic amphiphile is preferably a quaternary amino group. Also, the hydrophobic moiety preferably has 3–8 carbon atoms.

The specific examples of particularly preferable cationic amphiphiles will be given below.

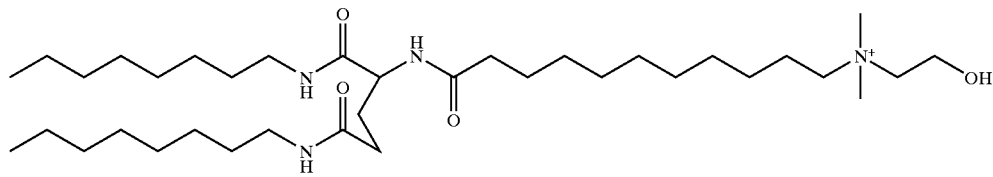

-continued

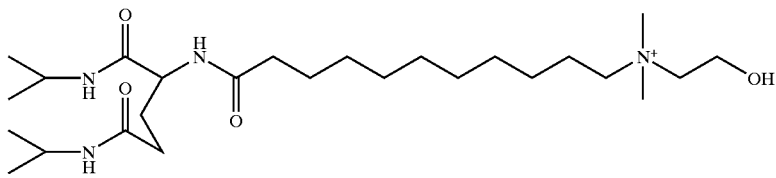

[B] Anion

The anion used in the present invention has a molecular weight of 90 or more, particularly 100–500. It is particularly preferably a so-called hydrophobic anion. The term "hydrophobic anion" used herein means an anion requiring large dissolution enthalpy, for instance, a large anion having a relatively weak electric field, and a large anion comprising a hydrophobic group such as an aromatic group.

By selecting anions suitable for cationic amphiphiles among the above anions, it is possible to form a stable supramolecular hydrogel. When the hydrophobic moiety of the cationic amphiphile is constituted by a branched alkyl group or an alkyl group having a small number of carbon atoms, precipitation does not occur even if a highly hydrophobic anion is added, preferable for forming a stable hydrogel.

The anions preferably used in the present invention included perchlorate ion, 2-naphthalenesulfonic acid and 9,10-dimethoxy-2-anthracenesulfonic acid. Particularly when the cationic amphiphile is

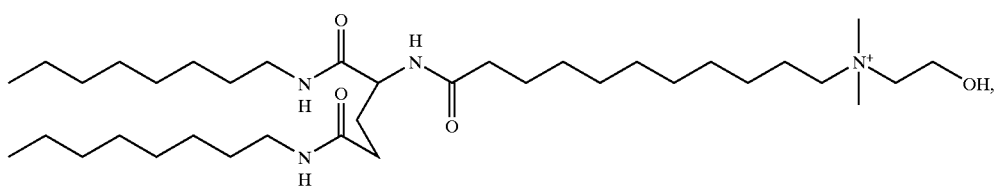

it is preferable to use perchloric ion, styrene sulfonic acid or 2-naphthalenesulfonic acid. Also, when the cationic amphiphile is

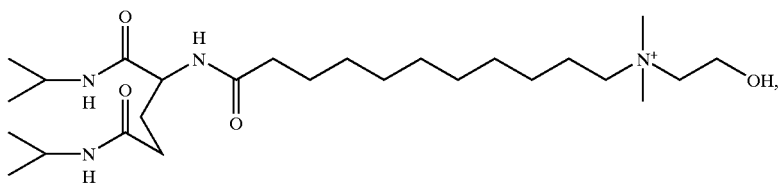

it is preferable to use 9,10-dimethoxy-2-anthracenesulfonic acid

[C] Formation of Supramolecular Hydrogel

The supramolecular hydrogel can be formed by adding an anion having a molecular weight of 90 or more to an aqueous dispersion of the cationic amphiphile.

The concentration of the cationic amphiphile in the aqueous dispersion is preferably 5–50 mM, particularly 10–20 mM. The anion is added in an amount of preferably 0.5–2 mol, particularly 1 mol, to 1 mol of the cationic amphiphile.

The formation of the supramolecular hydrogel of the present invention is based on the new idea that a hydrogel constituted by a nano-level supramolecular assembly is formed by the self-assembly of low-molecular weight compounds and hydrophobic anions. The supramolecular hydrogel of the present invention undergoes a reversible gel-sol transformation at a high temperature (up to 80° C.). Accordingly, by accurately controlling the nano-structure and properties of the supramolecular hydrogel through the chemical structure of constituent molecules and the characteristics of the supramolecular assemblies (phase transformation phenomenon, etc.), it can be applied for drug delivery systems, carriers for supporting enzyme proteins, artificial muscle, separation membranes, etc.

The present invention will be described in further detail referring to EXAMPLES below without intention of restricting the present invention thereto.

EXAMPLE

Cationic amphiphiles and anions shown in Table 1 were combined to form various hydrogels.

Each cationic amphiphile shown in Table 1 was mixed with water and subjected to ultrasonication for 1–2 minutes to prepare a uniform aqueous dispersion. After adding thereto various anions (Br$^-$, ClO$_4^-$, 2-naphthalenesulfonic acid, and 9,10-dimethoxy-2-anthracenesulfonic acid) in an equimolar amount, it was further subjected to ultrasonication for 1–2 minutes and then left to stand. The results are shown in Table 1.

TABLE 1

Amphiphiles

Compound 1

[Structure: Two C12 alkyl chains connected via amide bonds to a glutamine-like core, linked through an amide to a long alkyl chain terminating in a quaternary ammonium group $N^+(CH_3)_2$-CH$_2$CH$_2$OH]

($C_{12}$)

Compound 2

[Structure: Two C8 alkyl chains connected via amide bonds to a glutamine-like core, linked through an amide to a long alkyl chain terminating in a quaternary ammonium group $N^+(CH_3)_2$-CH$_2$CH$_2$OH]

($C_8$)

Compound 3

[Structure: Two isopropyl groups connected via amide bonds to a glutamine-like core, linked through an amide to a long alkyl chain terminating in a quaternary ammonium group $N^+(CH_3)_2$-CH$_2$CH$_2$OH]

($C_3$)

Anions

$Br^-$    $ClO_4^-$    [2-naphthalenesulfonate: naphthalene-$SO_3^-$]    [9,10-dimethoxy-2-anthracenesulfonate: anthracene with $OCH_3$ groups at 9,10-positions and $SO_3^-$]

| | $Br^-$ | $ClO_4^-$ | 2-naphthalenesulfonate | 9,10-dimethoxy-2-anthracenesulfonate |
|---|---|---|---|---|
| Compound 1 | Aqueous Dispersion of Bilayer Membrane (tested up to 20 mM) | Viscous Aqueous Dispersion of Bilayer Membrane (tested up to 20 mM) | Precipitation (10 mM) | Precipitation (10 mM) |
| Compound 2 | Aqueous Dispersion of Bilayer Membrane or Fibrous Micelle (tested up to 20 mM) | Hydrogel (10 mM) | Hydrogel (5 mM) | Precipitation (10 mM) |
| Compound 3 | Molecular Dispersion or Micellar Aggregates (tested up to 20 mM) | Uniform Aqueous Solution (tested up to 20 mM) | Hydrogel (not stable) (20 mM) | Hydrogel (20 mM) |

Figure 2:
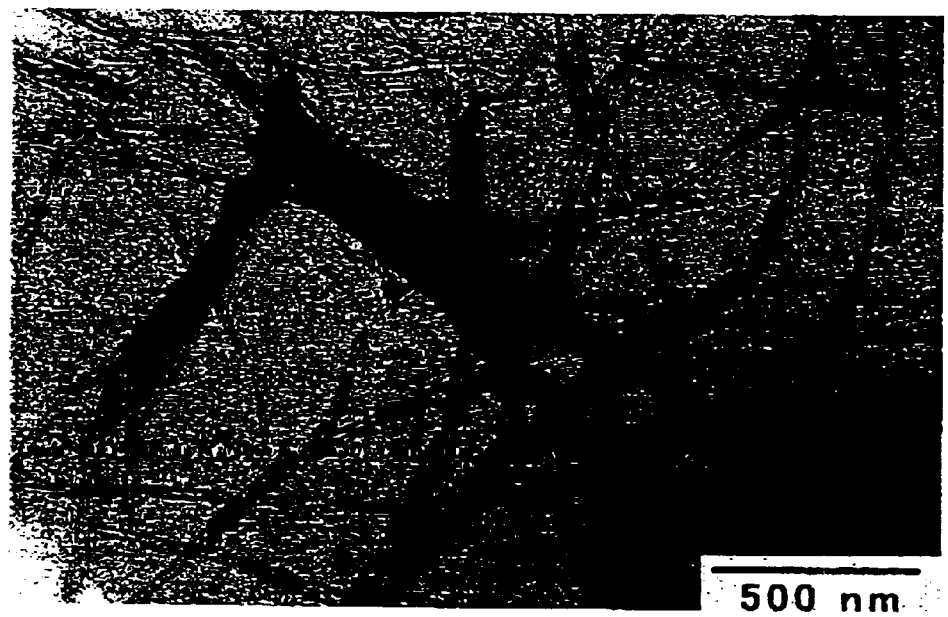
FIG. 2 is an electron photomicrograph of a sample comprising Compound 2 mixed with 2-naphthalenesulfonic acid (5 mM), which was diluted to 1 mM.
Figure 3:
FIG. 3 is an electron photomicrograph of a sample comprising Compound 3 mixed with 2-naphthalenesulfonic acid (20 mM), which was diluted to 2 mM.
Figure 4:
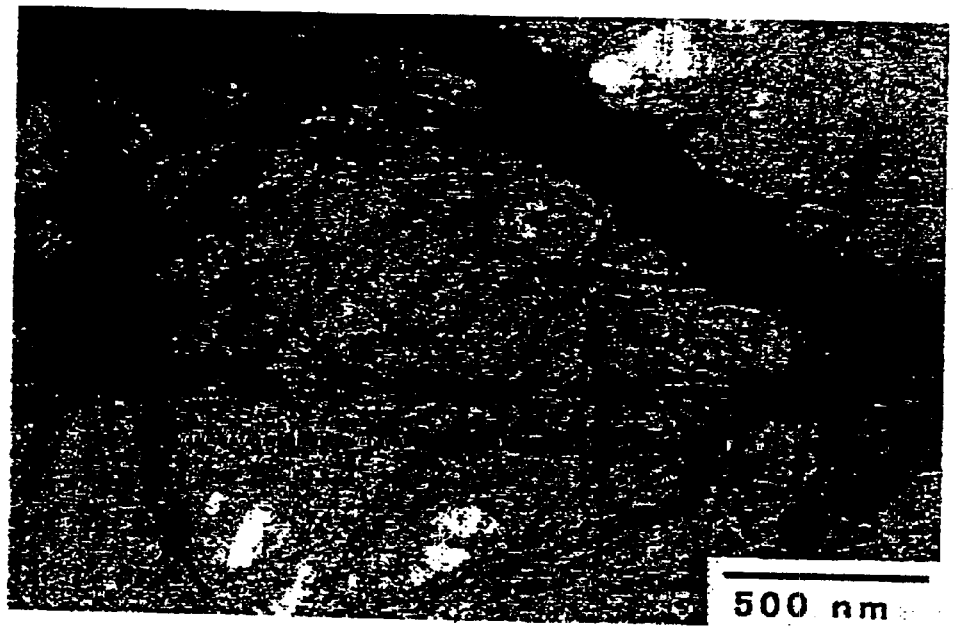
FIG. 4 is an electron photomicrograph of a sample comprising Compound 3 mixed with 9,10-dimethoxy-2-anthracenesulfonic acid (20 mM), which was diluted to 2 mM.

Compound 1 is a compound for forming a conventional bilayer membrane having a highly crystalline, hydrophobic moiety having 12 carbon atoms. Though a sample obtained by mixing Compound 1 with $ClO_4^-$ (up to 20 mM) provided a viscous aqueous solution (sol), all samples obtained by mixing Compound 1 with aromatic anions were precipitated. On the other hand, a sample obtained by mixing Compound 2 with $ClO_4^-$ (10 mM) or 2-naphthalenesulfonic acid (5 mM), and a sample obtained by mixing Compound 3 with 9,10-dimethoxy-2-anthracenesulfonic acid (20 mM) were not precipitated, forming uniform hydrogels After these samples were diluted to 1–2 mM, they were observed by electron microscopy to confirm that the sample obtained by mixing Compound 2 with $ClO_4^-$ (10 mM) had a network structure in which 3–10 fibrous aggregates of 8–10 nm in width and 3 μm or more in length were bundled (FIG. 1). With respect to the sample obtained by mixing Compound 2 with 2-naphthalenesulfonic acid (5 mM), fibrous aggregates of 8–16 nm in width and 2–3 μm in length were observed (FIG. 2). Further, with respect to the sample obtained by mixing Compound 3 with 9,10-dimethoxy-2-anthracenesulfonic acid (20 mM), a network structure having 5 or 6 bundled fibrous assemblies of about 6 nm in width and 3 μm or more in length was observed FIG. 4).

These aggregate forms are peculiar to the bilayer membranes, indicating that the addition of an anion having a molecular weight of 90 or more provided a fibrous cross-linked structure having a short-chain lipid (compound 2) or a branched lipid (Compound 3). Because the formation of such a hydrogel is not appreciated with the conventional bilayer-membrane-forming compound (Compound 1), it may be concluded that the formation of (i) a low-crystallinity, hydrophobic moiety, (ii) a hydrophilic moiety ion-paired with an anion (hydrophobic ion) having a molecular weight of 90 or more, and (iii) a developed hydrogen-bonded network are the condition for forming a supramolecular hydrogel. In view of the fact that the sample obtained by mixing Compound 2 with 9,10-dimethoxy-2-anthracenesulfonic acid (10 mM) was precipitated, while the sample obtained by mixing Compound 3 with 2-naphthalenesulfonic acid (20 mM) was less likely to be gelled, it has been found that the structural stability of the hydrogel largely depends on the molecular structures of both components, a lipid and a counter anion.

Next, the hydrogel formed by mixing Compound 2 with $ClO_4^-$ (10 mM) was spectroscopically evaluated with respect to thermal characteristics. The evaluation of the dependency of absorbance at 400 nm on temperature revealed that when the gel was heated, it was dissolved to form a sol in a temperature range of 60–75° C., and further heating rapidly turned it white. Because this change was reversible, white cloudiness disappeared by cooling and it returned to the sol and also to the original uniform hydrogel. In the DSC measurement of the gel, heat absorption was observed at 78° C. or higher, and endothermic peak was observed at 85° C. ($\Delta H$: 30 kJmol$^{-1}$). This endothermic peak corresponds to the white clouding of the solution, indicating that the sample undergoes not only a gel-sol transformation but also a large change in the aggregate state at higher temperatures. Similar gel-sol transformation and white clouding were observed also in the hydrogel formed by mixing Compound 2 with 2-naphthalenesulfonic acid.

Because the supramolecular hydrogel of the present invention has various properties and structural characteristics depending on the molecular structures of constituent components, various developments can be expected as a new hydrogel in the future.

As described above in detail, the supramolecular hydrogel of the present invention is formed by adding an anion having a molecular weight of 90 or more to an aqueous dispersion of a cationic amphiphile comprising a linear or branched alkyl group having 10 or less carbon atoms in a hydrophobic moiety, based on a new idea of forming a nano-level supramolecular hydrogel by complexation of a low-molecular weight compound and anions.

The supramolecular hydrogel of the present invention exhibits a reversible gel-sol transformation at high temperatures (up to 80° C.), the accurate control of its nano-structure and properties through the chemical structures of constituent molecules and the characteristics of the supramolecular assembly (phase transformation phenomenon, etc.) makes it possible to expect its application to drug delivery systems, carriers for supporting enzyme proteins, artificial muscle, separation membranes, etc.

What is claimed is:

1. A hydrogel formed by adding an anion having a molecular weight of 90 or more to an aqueous dispersion of a cationic amphiphile, wherein said cationic amphiphile is represented by either one of the following formulae:

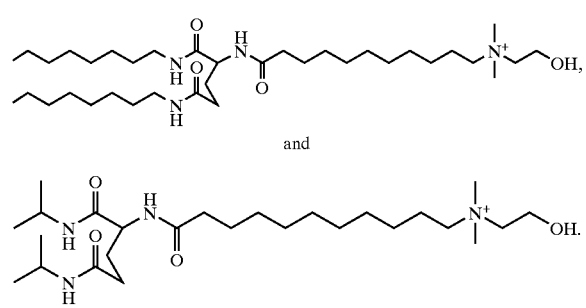

and

2. The hydrogel according to claim 1, wherein said anion is at least one selected from the group consisting of perchloric ion, styrene sulfonic acid, 2-naphthalenesulfonic acid and 9,10-dimethoxy-2-anthracenesulfonic acid.

3. The hydrogel according to claim 1, wherein said cationic amphiphile is

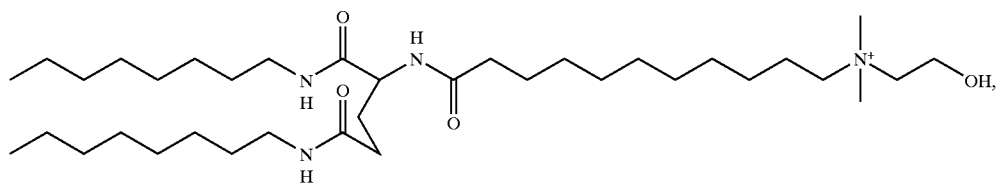

and said anion is perchloric ion, styrene sulfonic acid or 2-naphthalenesulfonic acid.

4. The hydrogel according to claim 1, wherein said cationic amphiphile is

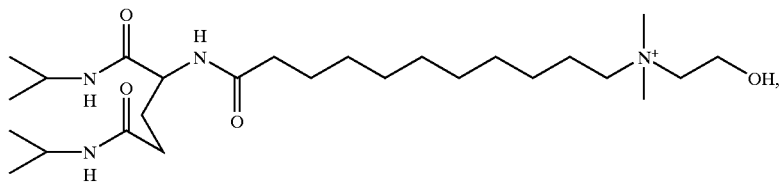
and said anion is 9,10-dimethoxy-2-anthracenesulfonic acid.
5. The hydrogel according to claim 1, wherein said hydrogel has a network having a bilayer membrane, nanofiber structure and undergoes a reversible gel-sol transformation.
* * * * *